United States Patent [19]
Fujii et al.

[11] 4,452,813
[45] Jun. 5, 1984

[54] SULFONATE DERIVATIVES, PROCESS FOR PREPARING SAME AND ANTILIPEMIC COMPOSITIONS CONTAINING THE DERIVATIVE

[75] Inventors: Setsuro Fujii, Toyonaka; Toshihiro Hamakawa, Naruto; Kazuo Ogawa, Tokushima; Yoshiyuki Muranaka, Tokushima; Sadao Hashimoto, Tokushima, all of Japan

[73] Assignee: Taiho Pharmaceutical Company Limited, Tokyo, Japan

[21] Appl. No.: 377,074

[22] Filed: May 11, 1982

[30] Foreign Application Priority Data

May 22, 1981 [JP] Japan ................................. 56-78530
Dec. 29, 1981 [JP] Japan ................................. 56-212950

[51] Int. Cl.³ .................. A61K 31/255; C07C 143/68
[52] U.S. Cl. .............................. 424/303; 260/456 P; 568/341; 568/343; 568/348
[58] Field of Search ..................... 260/456 P; 424/303

[56] References Cited

PUBLICATIONS

Fujii et al., Chem. Abstract, 96, 51,998W (1982), (Abstract of Fr. Demande FR2,475,041-8-7-1981.

Primary Examiner—Nicky Chan
Attorney, Agent, or Firm—Murray and Whisenhunt

[57] ABSTRACT

A sulfonate derivative represented by the formula

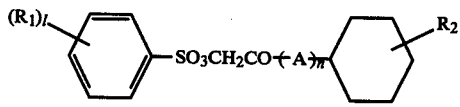

wherein $R_1$ is lower alkyl, lower alkoxy or halogen, l is an integer of from 0 to 3, n is 0 or 1, A is straight-chain or branched-chain alkylene having 1 to 4 carbon atoms, and $R_2$ is hydrogen or lower alkyl but, when n is 0 or 1 and A is straight-chain alkylene with 1 to 4 carbon atoms, is not hydrogen and the method for preparing the same.

2 Claims, No Drawings

SULFONATE DERIVATIVES, PROCESS FOR PREPARING SAME AND ANTILIPEMIC COMPOSITIONS CONTAINING THE DERIVATIVE

The present invention relates to novel sulfonate derivatives, a process for preparing the derivatives and antilipemic compositions containing the derivative.

The sulfonate derivatives of this invention are novel compounds which have not been disclosed in literature and which are represented by the formula (I)

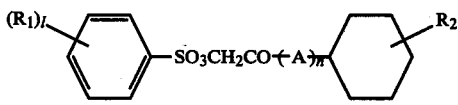

wherein $R_1$ is lower alkyl, lower alkoxy or halogen, l is an integer of from 0 to 3, n is 0 or 1, A is straight-chain or branched-chain alkylene having 1 to 4 carbon atoms, and $R_2$ is hydrogen or lower alkyl but, when n is 0 or 1 and A is straight-chain alkylene with 1 to 4 carbon atoms, is not hydrogen.

Examples of lower alkyl groups represented by $R_1$ and $R_2$ of the formula (I) are straight-chain or branched-chain lower alkyl groups having 1 to 6 carbon atoms, such as methyl, ethyl, propyl, isopropyl, butyl, pentyl, hexyl, etc. Examples of lower alkoxy groups represented by $R_1$ are those having 1 to 4 carbon atoms, such as methoxy, ethoxy, propyloxy, isopropyloxy, butoxy, etc. Examples of halogens are fluorine, chlorine, bromine and iodine. The substituent represented by $R_1$ can be present in any desired position on the benzene ring and is not limited to one in number but 2 or 3 substituents may be present.

Examples of straight-chain or branched-chain alkylene groups represented by A and having 1 to 4 carbon atoms are methylene, ethylene, trimethylene, tetramethylene, ethylmethylene, α-methylethylene, β-methylethylene, α-ethylmethylene, propylmethylene, etc. The substituent represented by $R_2$ can be present in any desired position on the cyclohexyl ring. The invention includes both cis- and trans-isomers which are present due to the cyclohexyl ring and the group $R_2$.

The novel sulfonate derivatives of the present invention include various compounds, such as those listed in Table 1 below.

Table 1

1-benzenesulfonyloxy-3-(4-isopropylcyclohexyl)-2-propanone,
1-benzenesulfonyloxy-4-methyl-4-cyclohexyl-2-pentanone,
1-(4-methylbenzenesulfonyloxy)-4-methyl-4-cyclohexyl-2-pentanone,
1-(2,4,6-trimethylbenzenesulfonyloxy)-4-methyl-4-cyclohexyl-2-pentanone,
1-benzenesulfonyloxy-3,3-dimethyl-4-cyclohexyl-2-butanone,
1-(4-methylbenzenesulfonyloxy)-3,3-dimethyl-4-cyclohexyl-2-butanone,
1-(2,4,6-trimethylbenzenesulfonyloxy)-3,3-dimethyl-4-cyclohexyl-2-butanone,
1-benzenesulfonyloxy-4-(4-methylcyclohexyl)-2-butanone,
1-(4-methylbenzenesulfonyloxy)-4-(4-methylcyclohexyl)-2-butanone,
1-benzenesulfonyloxy-3-methyl-3-(4-methylcyclohexy)-2-butanone,
1-(4-methylbenzenesulfonyloxy)-3-methyl-3-(4-methylcyclohexyl)-2-butanone,
1-benzenesulfonyloxy-3-methyl-3-cyclohexyl-2-butanone,
1-(4-methylbenzenesulfonyloxy)-3-methyl-3-cyclohexyl-2-butanone,
1-benzenesulfonyloxy-2-(4-n-propylcyclohexyl)-2-butanone,
1-benzenesulfonyloxy-3-(4-ethylcyclohexyl)-2-propanone,
1-benzenesulfonyloxy-4-(4-methylcyclohexyl)-2-pentanone,
1-(2,4,6-trimethylbenzenesulfonyloxy)-2-(4-sec-butylcyclohexyl)-2-ethanone,
1-benzenesulfonyloxy-3-cyclohexylmethyl-2-pentanone,
3-cyclohexylmethyl-1-(ethoxybenzenesulfonyloxy)-2-pentanone,
1-benzenesulfonyloxy-4-cyclohexyl-2-pentanone,
1-benzenesulfonyloxy-3-(2-methylcyclohexyl)-2-propanone,
1-benzenesulfonyloxy-3-(4-isopropylcyclohexyl)-2-propanone,
2-benzenesulfonyloxy-1-(4-ethylcyclohexyl)-1-ethanone,
2-benzenesulfonyloxy-1-(4-isopropylcyclohexyl)-1-ethanone,
1-(4-isobutylcyclohexyl)-2-(2,4,6-trimethylbenzenesulfonyloxy)-1-ethanone,
2-benzenesulfonyloxy-1-(4-isobutylcyclohexyl)-1-ethanone,
2-benzenesulfonyloxy-1-(4-sec-butylcyclohexyl)-1-ethanone and
2-(4-methylbenzenesulfonyloxy)-1-(4-sec-butylcyclohexyl)-1-ethanone.

The compounds of the formula (I) can be prepared, for example, by Process A, Process B or Process C described below.

Process A

A compound represented by the formula

wherein n, A and $R_2$ are as defined above is reacted with a compound of the formula

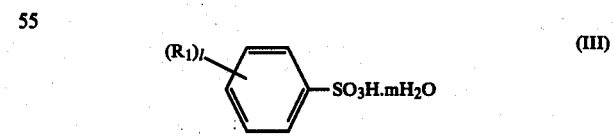

wherein $R_1$ and l are as defined above, and m is 0, 1 or 2.

The reaction of Process A is carried out usually in a solvent which is not particularly limited insofar as the solvent does not participate in the reaction. Examples of suitable solvents are ethers, such as dimethyl ether, diethyl ether, tetrahydrofuran and dioxane, nonprotonic solvents, such as acetonitrile, chloroform and dichloromethane, petroleum ether, ligroin, etc. The solvent is used usually in at least 2 times, preferably about 20 times, the amount of the compound II. The proportions of the compound (II) and the sulfonic acid compound (III) to be used are determined suitably. Usually at least one mole, preferably 1 to 1.5 moles, of the compound (III) is used per mole of the compound (II). The reaction proceeds advantageously usually at about $-10°$ to about 60° C., preferably about 0° C. to room temperature.

The compound (II) to be used as one of the starting materials in the above process can be prepared usually from a known compound (VI) and diazomethane by the following reaction.

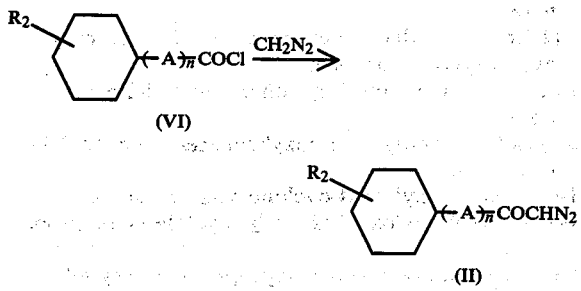

wherein n, $R_2$ and A are as defined above.

The reaction of the compound (VI) with diazomethane is conducted usually in a solvent. Examples of useful solvents are ethers, such as dimethyl ether, diethyl ether, tetrahydrofuran and dioxane, aprotic solvents, such as acetonitrile, chloroform and dichloromethane, petroleum ether, ligroin, etc. It is generally favorable to use at least about 2 moles of diazomethane per mole of the compound (VI). The reaction proceeds advantageously at about $-10°$ C. to room temperature. While the compound (II) obtained by the above reaction can be isolated by a usual method of separation such as chromatography or recrystallization, the reaction mixture can generally be used as it is for the reaction of Process A without isolation.

Process B

A compound represented by the formula

wherein X, n, A and $R_2$ are as defined above is reacted with a metallic salt of sulfonic acid represented by the formula

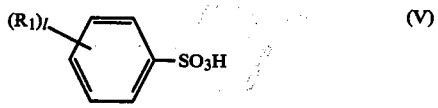

wherein $R_1$ and l are as defined above.

The reaction of Process B can be conducted advantageously in the absence of any solvent or in the presence of a suitable solvent which will not participate in the reaction. Examples of useful solvents are lower alcohols, such as methanol and ethanol, and polar solvents, such as acetone, acetonitrile, tetrahydrofuran, dioxane and dimethylformamide. The proportions of the compound (IV) and the compound (V) to be used are suitably determined. Usually at least one mole, preferably 1 to 1.5 moles, of the compound (V) is used per mole of the compound (IV). The reaction temperature, which can be determined also suitably, is advantageously room temperature to the boiling temperature of the solvent. Various metals are usable for metallic salts of the compound (V). Examples of preferred metals are silver, copper and like alkali metals and alkaline earth metals.

The compound (IV), one of the sulfonate derivatives of the present invention, used as one of the starting materials in Process B is a novel compound, which can be prepared by a known process, for example, by the following reaction

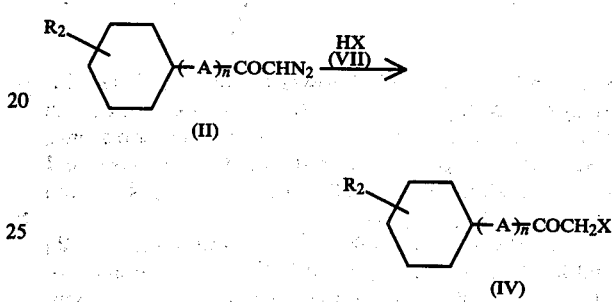

wherein $R_2$, A, n and X are as defined above.

Further the compound of the formula (IV) wherein X is iodine, namely compound (IV″), can also be prepared, for example, by the following reaction.

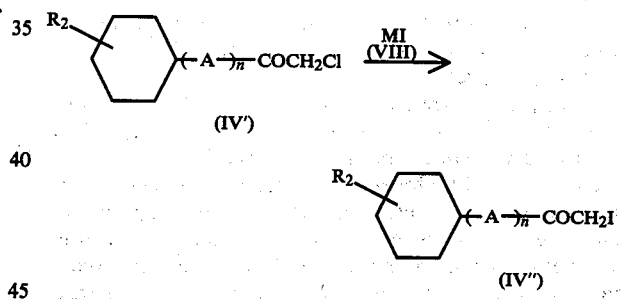

wherein n, $R_2$ and A are as defined above, and M is sodium, potassium or like alkali metal.

The reaction of the compound (II) with the compound (VII) is conducted usually in a solvent which will not participate in the reaction. Examples of useful solvents are diethyl ether, dioxane, tetrahydrofuran and like ethers. Usually at least one mole, preferably 1 to 1.5 moles, of the compound (VII) is used per mole of the compound (II). The reaction temperature is generally $-20°$ to 50° C., preferably 0° C. to room temperature.

The reaction of the compound (IV′) with the compound (VIII) is conducted usually without using any solvent or in a solvent which will not participate in the reaction. Exemplary of useful solvents are methanol, ethanol and like alcohols, tetrahydrofuran, dioxane and like polar solvents, acetone, etc. The proportions of the compound (IV′) and the compound (VIII), which may be determined suitably, are generally equimolar to achieve favorable results. The reaction temperature, which may be determined also suitably, is usually about 0° C. to the boiling point of the solvent, preferably room temperature to about 60° C. The compound (IV) or (IV″) obtained from either reaction can be isolated for use in Process B or is usable in the form of the resulting reaction mixture without isolation.

Process C

A hydroxyacetylcyclohexane derivative represented by the formula

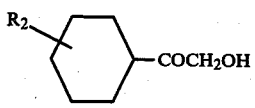
(IX)

wherein $R_2$ is as defined above is reacted with benzenesulfonyl chloride represented by the formula

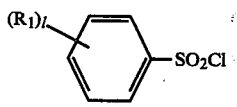
(X)

wherein $R_1$ and l are as defined above.

The reaction of Process C is conducted in a suitable solvent in the presence of a base serving as a dehydrochlorinating agent. Examples of useful solvents are those which will not participate in the reaction, such as dichloromethane, dichloroethane, chloroform and like hydrocarbon halides. Examples of useful bases are those usually used as dehydrochlorinating agents, such as pyridine, triethylamine, N,N-diisopropylethylamine, 1,8-diazabicyclo(5,4,0)-7-undecene (D.B.U.), etc. The base is used usually in an amount of 1 to 1.5 times based on the compound (X). The proportions of the hydroxyacetylcyclohexane derivative (IX) and benzenesulfonyl chloride (X) are not limited particularly but can be determined suitably. The compounds are used usually in the former to latter ratio of about 1:1 in mole, preferably in an equimolar ratio. The reaction proceeds satisfactorily at a temperature usually of about $-10°$ to about $50°$ C., preferably about $-5°$ to about $5°$ C.

The hydroxyacetylcyclohexane derivative (IX), one of the starting compounds to be used for Process C can be prepared by heating the compound obtained by Process A and represented by the formula

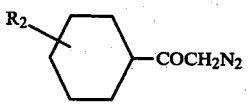
(II′)

wherein $R_2$ is as defined above in an aqueous solution of sulfuric acid. While the compounds of this invention include isomers of cis form and trans form, those of trans form only can be prepared by reacting the compound (XI) with sodium alkoxide in an alcohol to convert the cis form to a trans form (XII), brominating the same in usual manner and hydrolyzing the resulting bromine (XIII) in usual manner, for example in formic acid. Thus there is obtained an acetylcyclohexane derivative (IX′). This process is schematically illustrated below.

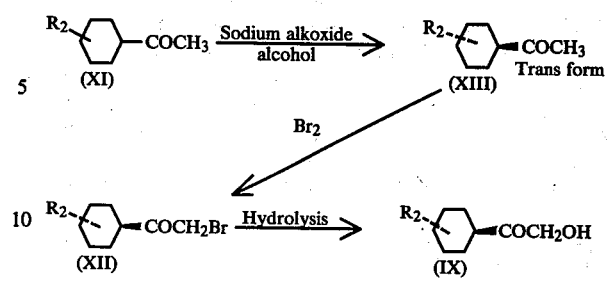

The compound of this invention prepared by Process A, B or C described above can be isolated by a usual method of separation, such as column chromatography, recrystallization or vacuum distillation.

The compounds of the invention have inhibitory activity on esterases and on chymotripsin and antilipemic activity and are useful as antilipemic agents, anti-inflammatory agents and immunity controlling agents. The present invention includes antilipemic compositions containing such novel sulfonate derivatives.

Hyperlipidemia is known to be a risk factor leading to various adult diseases, such as arteriosclerosis, cardio- and nephro-vascular diseases, diabetes, etc. The drugs for preventing or alleviating hyperlipidemia must have high safety because such drugs are likely to be used for a prolonged period of time in view of the nature of the disease. However, reports have been made on various side effects of nicotinic acid and derivatives thereof, dextran sulfate, and clofibrate and derivatives thereof heretofore widely used as antilipemic agents. Nicotinic acid and its derivatives, for example, produce side effects, such as pruritus and cutaneous flushing due to vasodilatation, gastrointestinal disorders, abnormalities in liver function and glucose intolerance. These drugs have many side effects further because they must be given at a large dose of at least 3 g/day.

Clofibrate, which is typical of widely used antilipemic agents, has recently been reported as having a carcinogenic activity as a serous side effect. Although animal tests or immunological investigations are being carried out by research institutes, the ultimate conclusions still remain to be made, so that clofibrate is clinically in limited use in various countires. In addition to the carcinogenic activity, clofibrate causes an increased sterol discharge, which reportedly increases the likelihood of gallstone formation. Thus the drug is likely to have another side effect.

The antilipemic compositions of the invention are characterized in that they are superior in antilipemic effect to nicotinic acid and derivatives thereof, dextran sulfate, and clofibrate and derivatives thereof heretofore known, very low in toxicity and usable for very wide applications with safety and assure higher safety than the conventional antilipemic agents.

The sulfonate compounds of the invention can be formulated into pharmaceutical preparations suited for various routes of administration. Examples of such preparations are tablets, capsules, granules, powders and liquids for oral administration, and suppositories for non-oral administration.

Examples of useful excipients for preparing tablets, capsules, granules and powders are lactose, sucrose, starch, talc, magnesium stearate, crystalline cellulose, methyl cellulose, carboxymethyl cellulose, glycerin, sodium alginate and gum arabic. Also useful for such preparations are binders, such as polyvinyl alcohol, polyvinyl ether, ethyl cellulose, gum arabic, shellac and sucrose, glazing agents, such as magnesium stearate and talc, and usual coloring agents and disintegrators. Tablets can be coated by a known method. Useful liquid preparations are in the form of aqueous or oily suspensions, solutions, syrups, elixir, etc. These preparations are produced by usual methods.

Examples of useful base materials for preparing suppositories are cacao butter, polyethylene glycol, lanolin, fatty acid triglyceride, witepsol (fat, trade mark of Dynamit Nobel A.G. of Germany), etc.

The dose of the drugs according to the invention can not be specifically defined but varies with the symptoms, body weight, age, etc. of the patient. Usually the active component of such drugs is given in an amount of about 50 to about 1500 mg/day for adults at a time or in two to four divided doses. The dose unit such as tablet or capsule preferably contains about 10 to about 1500 mg of the active component.

Table 2 shows typical diazo ketone compounds of the formula (II) useful for preparing the compounds of the invention. Table 3 shows typical chloromethyl ketone compounds of the formula (IV') which are similarly useful. Table 4 shows typical hydroxyacetylcyclohexane derivatives of the formula (IX). Tables 5-(1) and -(2) show typical examples of sulfonate derivatives of the invention represented by the formula (I). In the tables, "MS" stands for the result of mass spectrometry ($M^+$), and "H-NMR" the result of nuclear magnetic resonance absorption spectroscopy ($\delta$ ppm value) as measured in $CDCl_3$.

TABLE 2

$$N_2CHCO-(A)_{\overline{n}}-\text{cyclohexyl}-R_2$$

| Compound No. | $-(A)_{\overline{n}}-$ | $R_2$ | Physical property | MS ($M^+$) | H—NMR ($CDCl_3$) ($\delta$ ppm value) |
|---|---|---|---|---|---|
| A | —CHCH$_2$— <br> \|<br>CH$_3$ | H | Oily | 194 | 5.22 (s, 1H), <br> 2.63–2.25 (m, 1H), <br> 1.85–0.65 (m, 16H) |
| B | —CHCH$_2$— <br> \|<br>C$_2$H$_5$ | H | Oily | 208 | 5.20 (s, 1H), <br> 2.50–2.10 (br., m, 1H) <br> 2.00–0.65 (m, 18H) |
| C | —CH$_2$CH— <br> \|<br>CH$_3$ | H | Oily | 194 | 5.18 (s, 1H), <br> 2.50–0.75 (m, 17H) |
| D | —CH— <br> \|<br>C$_2$H$_5$ | 4-CH$_3$ | Oily | 208 | 5.20–5.08 (t, 1H), <br> 2.35–2.15 (m, 1H), <br> 2.10–0.65 (m, 18H) |
| E | —CH$_2$— | 4-CH$_3$ | Oily | 180 | 5.20 (s, 1H), 2.25 (t, 2H), <br> 2.10–0.75 (m, 13H) |
| F | —CH$_2$— | 2-CH$_3$ | Oily | 180 | 5.20 (s, 1H), <br> 2.32–2.00 (m, 2H), <br> 2.00–0.70 (m, 13H) |
| G | —CH$_2$— | 4-CH(CH$_3$)$_2$ | Oily | 208 | 5.20 (s, 1H), <br> 2.40–2.00 (m, 2H), <br> 2.00–0.70 (m, 17H) |
| H | — | 4-CH$_2$CH$_3$ | Oily | 180 | 5.28–5.21 (d, 1H), <br> 2.43–2.20 (br., m, 1H), <br> 2.20–0.70 (m, 14H) |
| I | — | 4-CH(CH$_3$)$_2$ <br> (cis form) | Oily | 194 | 5.31 (s, 1H), <br> 2.60–2.30 (b, 1H), <br> 2.15–0.95 (m, 10H) <br> 0.85 (d, 6H) |
| J | — | 4-CH(CH$_3$)$_2$ <br> (trans form) | 34–34.5 | 194 | 5.24 (s, 1H), <br> 2.36–0.96 (m, 11H), <br> 0.85 (d, 6H) |
| K | — | 4-CH$_2$CH(CH$_3$)$_2$ <br> (cis form) | Oily | 208 | 5.32 (s, 1H), <br> 2.56–2.20 (b, 1H), <br> 2.04–1.00 (m, 12H) <br> 0.85 (d, 6H) |

TABLE 2-continued

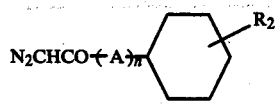

| Compound No. | $(A)_{\overline{n}}$ | R$_2$ | Physical property | MS (M$^+$) | H—NMR (CDCl$_3$) (δ ppm value) |
|---|---|---|---|---|---|
| L | — | 4-CH$_2$CH(CH$_3$)$_2$ (trans form) | 36–37 | 208 | 5.27 (s, 1H), 2.38–0.70 (m, 13H), 0.89 (d, 6H) |
| M | — | 4-CH(CH$_3$)CH$_2$CH$_3$ (cis form) | Oily | 208 | 5.33 (s, 1H), 2.60–2.30 (b, 1H), 2.14–0.65 (m, 18H) |
| N | — | 4-CH(CH$_3$)CH$_2$CH$_3$ (trans form) | Oily | 208 | 5.24 (s, 1H), 2.35–0.60 (m, 19H) |
| O | — | 4-C(CH$_3$)$_3$ (cis form) | 32.5–33 | 208 | 5.36 (s, 1H), 2.64–2.40 (b, 1H), 2.28–0.65 (m, 9H), 0.82 (s, 9H) |
| P | — | 4-C(CH$_3$)$_3$ (trans form) | 57.5–58.5 | 208 | 5.25 (s, 1H), 2.32–0.60 (m, 10H), 0.84 (s, 9H) |

TABLE 3

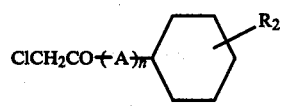

| Compound No. | $(A)_{\overline{n}}$ | R$_2$ | B.P. (°C./mm Hg) | MS (M$^+$) | H—NMR (CDCl$_3$) (δ ppm value) |
|---|---|---|---|---|---|
| i | —CH(C$_2$H$_5$)CH$_2$— | H | 108/1 | 216 | 4.10 (s, 2H), 2.95–2.55 (m, 1H), 1.90–0.60 (m, 18H) |
| ii | —CH$_2$CH(CH$_3$)— | H | 118–119/1 | 202 | 4.04 (s, 2H), 2.82–2.35 (m, 2H), 2.20–0.75 (m, 15H) |
| iii | —CH$_2$— | 4-CH$_3$ | 108–108.5/2 | 188 | 4.05 (s, 2H), 2.65–2.35 (q, 2H), 2.30–0.70 (m, 13H) |
| iv | — | 4-CH(CH$_3$)$_2$ | 105/1 | 202 | 4.13 (s, 2H), 2.90–2.65 (br., 1H), 2.20–0.70 (m, 16H) |

TABLE 4

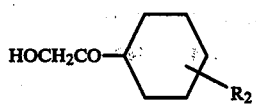

| Compound No. | R$_2$ | M.P. (°C.) or B.P. (°C./mm Hg) | Yield (%) | Elementary analysis or NMR | calculated | found |
|---|---|---|---|---|---|---|
| a | 4-CH(CH$_3$)$_2$ (trans form) | 43–44 | 80.2 | C | 71.70 | 71.51 |
| | | | | H | 10.94 | 10.92 |
| b | 4-CH$_2$CH(CH$_3$)$_2$ (trans form) | 65.5–66.5 | 78.7 | C | 72.68 | 72.47 |
| | | | | H | 11.18 | 11.30 |

TABLE 4-continued

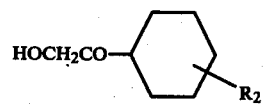

| Compound No. | $R_2$ | M.P. (°C.) or B.P. (°C./mm Hg) | Yield (%) | Elementary analysis or NMR calculated | found |
|---|---|---|---|---|---|
| c | 4-CHCH$_2$CH$_3$<br>\|<br>CH$_3$<br>(trans form) | 117–123/2–3<br><br>mm Hg | 55.0 | 4.30 (d, 2H), 3.16 (t, 1H),<br><br>2.66–2.30 (b, 1H),<br>2.10–0.70 (m, 18H) | |
| d | 4-C(CH$_3$)$_3$<br>(trans form) | 64–65.5 | 72.6 | C  72.68<br>H  11.18 | 72.54<br>11.45 |

TABLE 5 - (1)

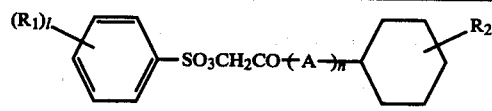

| Compound No. | $(R_1)_l$ | $(A)_n$ | $R_2$ | B.P. (°C.) or physical property | MS ($M^+$) | Yield (%) |
|---|---|---|---|---|---|---|
| 1 | H | —CHCH$_2$—<br>\|<br>CH$_3$ | H | 51–52 | 324 | 74.8 |
| 2 | 4-CH$_3$ | —CHCH$_2$—<br>\|<br>CH$_3$ | H | 50–51 | 338 | 71.0 |
| 3 | 4-OCH$_3$ | —CHCH$_2$—<br>\|<br>CH$_3$ | H | Oily | 354 | 78.5 |
| 4 | 4-OC$_2$H$_5$ | —CHCH$_2$—<br>\|<br>CH$_3$ | H | 32–33 | 368 | 67.8 |
| 5 | H | —CHCH$_2$—<br>\|<br>C$_2$H$_5$ | H | Oily | 338 | 73.5 |
| 6 | 4-OCH$_3$ | —CHCH$_2$—<br>\|<br>C$_2$H$_5$ | H | Oily | 368 | 73.0 |
| 7 | 4-OC$_2$H$_5$ | —CHCH$_2$—<br>\|<br>C$_2$H$_5$ | H | 42–43 | 382 | 69.5 |
| 8 | H | —CH$_2$CH—<br>\|<br>CH$_3$ | H | Oily | 324 | 71.3 |
| 9 | 4-CH$_3$ | —CH$_2$CH—<br>\|<br>CH$_3$ | H | Oily | 338 | 79.5 |
| 10 | 4-OCH$_3$ | —CH$_2$CH—<br>\|<br>CH$_3$ | H | 52–53 | 354 | 76.7 |
| 11 | 4-OC$_2$H | —CH$_2$CH—<br>\|<br>CH$_3$ | H | 25 | 368 | 70.5 |
| 12 | 2,4,6-CH$_3$ | —CH$_2$CH—<br>\|<br>CH$_3$ | H | Oily | 366 | 78.5 |

TABLE 5 - (1)-continued $$(R_1)_l\text{-C}_6\text{H}_{4-l}\text{-SO}_3\text{CH}_2\text{CO}(\text{-A-})_n\text{-C}_6\text{H}_{10}\text{-R}_2$$

| Compound No. | $(R_1)_l$ | $(\text{-A-})_n$ | $R_2$ | B.P. (°C.) or physical property | MS (M+) | Yield (%) |
|---|---|---|---|---|---|---|
| 13 | 4-CH$_3$ | −CH(C$_2$H$_5$)− | 4-CH$_3$ | Oily | 352 | 68.8 |
| 14 | 4-OC$_2$H$_5$ | −CH(C$_2$H$_5$)− | 4-CH$_3$ | Oily | 382 | 67.3 |
| 15 | 4-CH$_3$ | −CH$_2$− | 4-CH$_3$ | 42–43.5 | 324 | 74.2 |
| 16 | 4-OC$_2$H$_5$ | −CH$_2$− | 4-CH$_3$ | 33–34 | 354 | 79.3 |
| 17 | H | −CH$_2$− | 2-CH$_3$ | Oily | 310 | 77.4 |
| 18 | 4-CH$_3$ | −CH$_2$− | 2-CH$_3$ | Oily | 324 | 72.3 |
| 19 | 4-OC$_2$H$_5$ | −CH$_2$− | 2-CH$_3$ | Oily | 354 | 69.5 |
| 20 | 2,5-Cl | −CH$_2$− | 2-CH$_3$ | Oily | 378 | 65.3 |
| 21 | H | −CH$_2$− | 4-CH(CH$_3$)$_2$ | 45.5–46 | 338 | 79.5 |
| 22 | H | — | 4-C$_2$H$_5$ | Oily | 310 | 74.7 |
| 23 | 4-OC$_2$H$_5$ | — | 4-C$_2$H$_5$ | 53–53.5 | 354 | 71.3 |
| 24 | H | — | 4-CH(CH$_3$)$_2$ (cis form) | 42–43 | 324 | 83.8 |
| 25 | H | — | 4-CH(CH$_3$)$_2$ (trans form) | 48–49 | 324 | 77.8 |
| 26 | 4-OC$_2$H$_5$ | — | 4-CH(CH$_3$)$_2$ (cis form) | 71–72 | 368 | 73.0 |
| 27 | 4-OC$_2$H$_5$ | — | 4-CH(CH$_3$)$_2$ (trans form) | 80–81 | 368 | 69.5 |
| 28 | 2,4,6-CH$_3$ | — | 4-CH(CH$_3$)$_2$ (cis form) | 44.5–45.5 | 366 | 75.5 |
| 29 | 2,4,6-CH$_3$ | — | 4-CH(CH$_3$)$_2$ (trans form) | 66–67 | 366 | 78.0 |
| 30 | H | — | 4-CH$_2$CH(CH$_3$)$_2$ (cis form) | 36–37 | 338 | 74.0 |

TABLE 5 - (1)-continued $$(R_1)_l\text{-}C_6H_4\text{-}SO_3CH_2CO\text{-}(A)_n\text{-}C_6H_{10}\text{-}R_2$$

| Compound No. | $(R_1)_l$ | $-(A)_n-$ | $R_2$ | B.P. (°C.) or physical property | MS $(M^+)$ | Yield (%) |
|---|---|---|---|---|---|---|
| 31 | H | — | 4-CH$_2$CH(CH$_3$)$_2$<br>(trans form) | 49–49.5 | 338 | 77.5 |
| 32 | H | — | 4-CHCH$_2$CH$_3$<br>\|<br>CH$_3$<br>(cis form) | 29.5–30 | 338 | 68.5 |
| 33 | H | — | 4-CHCH$_2$CH$_3$<br>\|<br>CH$_3$<br>(trans form) | Oily | 338 | 72.0 |
| 34 | H | — | 4-C(CH$_3$)$_3$<br>(cis form) | 78.5–79.5 | 338 | 75.0 |
| 35 | H | — | 4-C(CH$_3$)$_3$<br>(trans form) | 73–74 | 338 | 78.5 |
| 36 | 4-CH$_3$ | — | 4-C(CH$_3$)$_3$<br>(cis form) | 115–116 | 352 | 67.5 |
| 37 | 4-CH$_3$ | — | 4-C(CH$_3$)$_3$<br>(trans form) | 89.5–90 | 352 | 78.0 |
| 38 | 4-CH$_3$ | — | 4-CHCH$_2$CH$_3$<br>\|<br>CH$_3$<br>(trans form) | 42–43 | 352 | 73.0 |

TABLE 5 - (2)

| Compound No. | H—NMR (CDCl$_3$) (δ ppm value) | | Elementary analysis (%) calculated | found |
|---|---|---|---|---|
| 1 | 8.00–7.40 (m, 5H), 4.61 (s, 2H),<br>2.90–2.62 (m, 1H), 1.80–0.70 (m, 16H) | C<br>H | 62.94<br>7.46 | 63.04<br>7.55 |
| 2 | 7.78 (d, 2H), 7.30 (d, 2H),<br>4.59 (s, 2H), 2.95–2.60 (m, 1H),<br>2.44 (s, 3H), 1.80–0.75 (m, 16H) | C<br>H | 63.88<br>7.74 | 63.94<br>7.91 |
| 3 | 7.81 (d, 2H), 6.97 (d, 2H),<br>4.56 (s, 2H), 3.88 (s, 3H),<br>2.92–2.60 (m, 1H), 1.85–0.70 (m, 16H) | | — | |
| 4 | 7.81 (d, 2H), 6.97 (d, 2H),<br>4.58 (s, 2H), 4.10 (q, 2H),<br>2.92–2.60 (m, 1H), 1.80–0.70 (m, 19H) | C<br>H | 61.93<br>7.66 | 61.58<br>7.79 |
| 5 | 8.05–7.35 (m, 5H), 4.58 (s, 2H),<br>2.80–2.40 (m, 1H), 1.90–0.60 (m, 18H) | | — | |
| 6 | 7.84 (d, 2H), 6.98 (d, 2H),<br>4.53 (s, 2H), 3.88 (s, 3H),<br>2.82–2.42 (m, 1H), 1.85–0.65 (m, 18H) | | — | |
| 7 | 7.84 (d, 2H), 6.98 (d, 2H),<br>4.55 (s, 2H), 4.08 (q, 2H),<br>2.80–2.45 (m, 1H), 1.90–0.70 (m, 21H) | C<br>H | 62.80<br>7.91 | 62.93<br>7.98 |
| 8 | 8.00–7.32 (m, 5H), 4.48 (s, 2H),<br>2.65–2.20 (m, 2H), 2.10–0.70 (m, 15H) | | — | |
| 9 | 7.81 (d, 2H), 7.34 (d, 2H),<br>4.44 (s, 2H), 2.43 (s, 3H),<br>2.65–2.20 (m, 2H), 2.10–0.80 (m, 12H),<br>0.71 (d, 3H) | | — | |
| 10 | 7.81 (d, 2H), 6.98 (d, 2H),<br>4.45 (s, 2H), 3.90 (s, 3H),<br>2.68–2.22 (m, 2H), 2.10–0.90 (m, 12H),<br>0.81 (d, 3H) | C<br>H | 60.99<br>7.39 | 61.36<br>7.40 |
| 11 | 7.82 (d, 2H), 6.98 (d, 2H),<br>4.43 (s, 2H), 4.04 (q, 2H),<br>2.65–2.20 (m, 2H), 2.10–0.65 (m, 18H) | | — | |
| 12 | 6.91 (s, 2H), 4.39 (s, 2H),<br>2.63 (s, 6H), 2.29 (s, 3H),<br>2.55–2.15 (m, 2H), 2.10–0.90 (m, 12H),<br>0.71 (d, 3H) | | — | |

TABLE 5 - (2)-continued

| Compound No. | H—NMR (CDCl₃) (δ ppm value) | | Elementary analysis (%) calculated | found |
|---|---|---|---|---|
| 13 | 7.90–7.60 (m, 2H), 7.42–7.19 (m, 2H), 4.51–4.40 (t, 2H), 2.42 (s, 3H), 2.70–2.28 (m, 1H), 1.90–0.65 (m, 18H) | | — | |
| 14 | 7.95–7.65 (m, 2H), 7.10–6.80 (m, 2H), 4.55–4.40 (t, 2H), 4.06 (q, 2H), 2.61–2.20 (m, 1H), 1.90–0.65 (m, 21H) | | — | |
| 15 | 7.80 (d, 2H), 7.33 (d, 2H), 4.44 (s, 2H), 2.44 (s, 3H), 2.40–2.20 (m, 2H), 2.15–0.75 (m, 13H) | C H | 62.94 7.46 | 63.25 7.45 |
| 16 | 7.95–7.72 (q, 2H), 7.08–6.88 (q, 2H), 4.42 (s, 2H), 4.06 (q, 2H), 2.50–2.21 (q, 2H), 2.15–0.80 (m, 16H) | C H | 60.99 7.39 | 61.06 7.35 |
| 17 | 7.98–7.35 (m, 5H), 4.51 (s, 2H), 2.40–2.24 (m, 2H), 2.22–0.90 (m, 10H), 0.80 (d, 3H) | | — | |
| 18 | 7.74 (d, 2H), 7.29 (d, 2H), 4.47 (s, 2H), 2.45 (s, 3H), 2.40–2.25 (m, 2H), 2.20–1.00 (m, 10H), 0.80 (d, 3H) | | — | |
| 19 | 7.88–7.68 (m, 2H), 7.02–6.85 (m, 2H), 4.45 (s, 2H), 4.08 (q, 2H), 2.42–2.22 (m, 2H), 2.22–1.00 (m, 13H), 0.80 (d, 3H) | | — | |
| 20 | 8.00 (d, 1H), 7.50 (d, 2H), 4.68 (s, 2H), 2.50–2.30 (m, 2H), 2.20–0.95 (m, 10H), 0.82 (d, 3H) | | — | |
| 21 | 8.10–7.48 (m, 5H), 4.50, 4.52 (s, s, 1H), 2.55–2.28 (q, 2H), 2.00–0.60 (m, 17H) | C H | 63.88 7.74 | 63.57 7.93 |
| 22 | 8.00–7.35 (m, 5H), 4.62 (s, 2H), 2.70–2.20 (br., m, 1H), 2.00–0.60 (m, 14H) | | — | |
| 23 | 7.82 (d, 2H), 6.98 (d, 2H), 4.59 (s, 2H), 4.10 (q, 2H), 2.75–2.30 (br., 1H), 2.00–0.70 (m, 17H) | C H | 60.99 7.39 | 61.01 7.32 |
| 24 | 8.10–7.50 (m, 5H), 4.65 (s, 2H), 2.82–2.58 (b, 1H), 2.10–0.94 (m, 10H), 0.82 (d, 6H) | C H | 62.94 7.46 | 62.76 7.51 |
| 25 | 8.10–7.50 (m, 5H), 4.63 (s, 2H), 2.64–2.20 (b, 1H), 2.00–0.94 (m, 10H), 0.85 (d, 6H) | C H | 62.94 7.46 | 62.78 7.39 |
| 26 | 7.86 (d, 2H), 6.99 (d, 2H), 4.59 (s, 1H), 4.11 (q, 2H), 2.86–2.58 (b, 1H), 2.10–0.94 (m, 10H), 1.45 (t, 3H), 0.82 (d, 6H) | C H | 61.93 7.66 | 61.92 7.77 |
| 27 | 7.85 (d, 2H), 6.99 (d, 2H), 4.58 (s, 1H), 4.11 (q, 2H), 2.61–2.28 (b, 1H), 2.00–0.95 (m, 10H) | C H | 61.93 7.66 | 61.84 7.65 |
| 28 | 6.98 (s, 2H), 4.56 (s, 2H), 2.88–2.60 (b, 1H), 2.64 (s, 6H), 2.31 (s, 3H), 2.10–0.95 (m, 10H), 0.82 (d, 6H) | C H | 65.54 8.25 | 65.20 8.20 |
| 29 | 6.99 (s, 2H), 4.54 (s, 2H), 2.64 (s, 6H), 2.64–2.30 (b, 1H), 2.32 (s, 3H), 2.04–0.95 (m, 10H), 0.85 (d, 6H) | C H | 65.54 8.25 | 65.48 8.34 |
| 30 | 8.10–7.45 (m, 5H), 4.66 (s, 2H), 2.80–2.50 (b, 1H), 2.00–0.95 (m, 2H), 0.83 (d, 6H) | C H | 63.88 7.74 | 63.89 7.98 |
| 31 | 8.10–7.42 (m, 5H), 4.64 (s, 2H), 2.66–2.28 (t, 1H), 2.00–0.64 (m, 12H), 0.84 (d, 6H) | C H | 63.88 7.74 | 64.20 7.97 |
| 32 | 8.10–7.44 (m, 5H), 4.65 (s, 2H), 2.84–2.58 (b, 1H), 2.10–0.60 (m, 18H) | C H | 63.88 7.74 | 63.68 8.05 |
| 33 | 8.10–7.45 (m, 5H), 4.63 (s, 2H), 2.68–2.20 (m, 1H), 2.10–0.70 (m, 18H) | | — | |
| 34 | 8.08–7.48 (m, 5H), 4.66 (s, 2H), 2.86–2.64 (b, 1H), 2.30–0.78 (m, 9H), 0.79 (s, 9H) | C H | 63.88 7.74 | 63.66 8.03 |
| 35 | 8.08–7.50 (m, 5H), 4.63 (s, 2H) 2.64–2.28 (b, 1H), 2.04–0.60 (m, 9H), 0.84 (s, 9H) | C H | 63.88 7.74 | 63.64 8.85 |
| 36 | 7.82 (d, 2H), 7.35 (d, 2H), 4.62 (s, 2H), 2.84–2.60 (b, 1H), 2.45 (s, 3H), 2.24–0.60 (m, 9H), 0.79 (s, 9H) | C H | 64.74 8.01 | 64.96 8.09 |
| 37 | 7.82 (d, 2H), 7.36 (d, 2H), 4.59 (s, 2H), 2.46 (s, 3H), 2.68–2.28 (b, 1H), 2.10–0.60 (m, 9H), 0.84 (s, 9H) | C H | 64.74 8.01 | 65.10 8.22 |

TABLE 5 - (2)-continued

| Compound No. | H—NMR (CDCl₃) (δ ppm value) | Elementary analysis (%) calculated | found |
|---|---|---|---|
| 38 | 7.85 (d, 2H), 7.38 (d, 2H), 4.60 (s, 2H), 2.47 (s, 3H), 2.69–2.28 (b, 1H), 2.08–0.78 (m, 18H) | C 64.74 | 64.86 |

Given below are reference examples in which the compounds listed in Tables 2 to 4 are prepared.

REFERENCE EXAMPLE 1

A 100 ml quantity of diazomethane ether solution (containing 2.8 g of diazomethane) is prepared from 10 g of N-methyl-nitrosourea. A 3.0 g quantity of α-methyl-β-cyclohexyl-propionyl chloride is added dropwise to the ether solution with ice cooling, the mixture is thereafter stirred for 30 minutes, and the excess of diazomethane is removed from the reaction mixture by passing nitrogen gas through the mixture at room temperature. The mixture is distilled in a vacuum, quantitatively giving 1-diazo-3-methyl-4-cyclohexyl-2-butanone (Compound A) in the form of a pale yellow oil.

REFERENCE EXAMPLE 2

Compounds B to H are prepared in the same manner as in Reference Example 1.

REFERENCE EXAMPLE 3

A 25.0 g quantity of 4-isopropylbenzoic acid is hydrogenated in acetic acid in the presence of 1.0 g of platinum oxide of the Adams type at room temperature and 100 atm. to give 23.0 g of 4-isopropylcyclohexanone-1-carboxylic acid boiling at 131° to 134° C./1 mm Hg (yield: 88.8%). (H-NMR analysis shows that the cis form and the trans form are in the ratio of about 3:1)

A 23.0 g quantity of 4-isopropyl-cyclohexanone-1-carboxylic acid is treated with thionyl chloride, giving 23.0 g of 4-isopropylcyclohexanone-1-carbonyl chloride boiling at 140° to 142° C./45 mm Hg (yield: 90.1%).

A 6.0 g quantity of 4-isopropylcyclohexanone-1-carbonyl chloride is reacted with an excess of diazomethane, quantitatively giving 1-diazo-2-(4-isopropylcyclohexyl)-2-ethanone.

The 1-diazo-2-(4-isopropylcyclohexyl)-2-ethanone (mixture of cis form and trans form in the ratio of 3:1) is separated and purified by silica gel column chromatography (developer solvent: chloroform), giving 3.5 g of cis-1-diazo-2-(4-isopropylcyclohexyl)-2-ethanone (Compound I) in the form of a pale yellow oil as the first fraction and subsequently affording 1.2 g of trans-1-diazo-2-(4-isopropylcyclohexyl)-2-ethanone (Compound J).

REFERENCE EXAMPLE 4

Compounds K to P listed in Table 2 are prepared in the same manner as in Reference Example 3.

REFERENCE EXAMPLE 5

A 15 g quantity of 1-diazo-3-ethyl-4-cyclohexyl-2-butanone (Compound B) is dissolved in 200 ml of ether, and the solution is caused to absorb an excess of dry hydrogen chloride gas with ice cooling and stirred until evolution of nitrogen ceases. The reaction mixture is washed with water, and the ethereal layer is dried over anhydrous sodium sulfate. The dried layer is distilled in a vacuum to remove the solvent. The residue is distilled in a vacuum, affording 15.5 g of 1-chloro-3-ethyl-4-cyclohexyl-2-butanone (Compound i) boiling at 108° C./1 mm Hg (yield: 92.8%).

REFERENCE EXAMPLE 6

Compounds ii to iv listed in Table 3 are prepared in the same manner as in Reference Example 5.

REFERENCE EXAMPLE 7

A 12 g quantity of cis-trans mixture of 1-acetyl-4-isopropylcyclohexane and sodium methoxide in an amount equimolar to the mixture are heated in 150 ml of methanol for 6 hours with stirring. The reaction mixture is distilled in a vacuum to remove the solvent, 50 ml of water is added to the residue, and the resulting solution is subjected to extraction with 50 ml of ether three times. The extract is washed with water, dried over anhydrous sodium sulfate and thereafter distilled in a vacuum to remove the solvent. The residue is distilled in a vacuum, giving 9 g of trans-1-acetyl-4-isopropylcyclohexane boiling at 109° to 113° C./18–19 mm Hg.

An 8 g quantity of the product is dissolved in 130 ml of methanol. Bromine (8 g) is added to the solution at a time, and the mixture is stirred for 4 hours. The reaction mixture is neutralized with sodium hydrogencarbonate and then distilled in a vacuum to remove the solvent. With addition of 30 ml of water, the residue is subjected to extraction with 100 ml of ether three times. The extract is washed with water, dried over anhydrous sodium sulfate and thereafter distilled in a vacuum to remove the solvent. The residue is distilled in a vacuum, affording 8.5 g of trans-1-(bromoacetyl)-4-isopropylcyclohexane boiling at 113 to 115/2 mm Hg.

In 60 ml of methanol is dissolved 4.5 g of potassium hydroxide, 6.6 g of ethyl formate is added to the solution with ice cooling, and the mixture is heated for 2 hours with stirring and thereafter cooled again. The trans-1-(bromoacetyl)-4-isopropylcyclohexane (10 g) obtained from the above reaction is added to the mixture, and the resulting mixture is heated for 10 hours with stirring. The solvent is distilled off from the reaction mixture in a vacuum, water is added to the residue, and the solution is subjected to extraction with 100 ml of ether twice. The extract is dried over anhydrous sodium sulfate, then distilled in a vacuum to remove the solvent, and the resulting residue is recrystallized from petroleum ether, affording 6 g of trans-1-(hydroxyacetyl)-4-isopropylcyclohexane (Compound a) melting at 43° to 44° C.

REFERENCE EXAMPLE 8

Compounds b, c and d listed in Table 4 are prepared in the same manner as in Reference Example 7.

EXAMPLE 1

Two grams of 1-diazo-3-methyl-4-cyclohexyl-2-butanone is dissolved in 50 ml of ether, 2.1 g of benzene-sulfonic acid monohydrate is slowly added to the solution at room temperature, and the mixture is stirred until evolution of nitrogen ceases. After the reaction, the ethereal layer is washed with water, dired over anhydrous sodium sulfate and distilled in a vacuum to remove the solvent. The resulting oily product is separated and purified by column chromatography (silica gel, developer solvent: chloroform), giving 2.5 g of 1-benzenesulfonyloxy-4-cyclohexyl-3-methyl-2-butanone (Compound 1) melting at 51° to 52° C. (yield: 74.8%).

EXAMPLE 2

Compounds 2 to 4 and 6 are prepared in the same manner as in Example 1.

EXAMPLE 3

A 2.0 g quantity of 1-diazo-4-cyclohexyl-2-pentanone (Compound C) is dissolved in 50 ml of dioxane, 2.3 g of p-methoxybenzenesulfonic acid is slowly added to the solution at room temperature, and the mixture is stirred until evolution of nitrogen ceases. The reaction mixture is distilled in a vacuum to remove the solvent, and the residue is subjected to extraction with 50 ml of ether. The extract is washed with water, dried over anhydrous sodium sulfate and then distilled in a vacuum to remove the solvent. The resulting oily product is subjected to silica gel column chromatography (developer solvent: chloroform) for separation and purification, giving 2.8 g of 4-cyclohexyl-1-(4-methoxybenzenesulfonyloxy)2-pentanone (Compound 10) melting at 52° to 53° C. (yield: 76.7%).

EXAMPLE 4

Compounds 11 to 14 are prepared in the same manner as in Example 3.

EXAMPLE 5

A 1.8 g quantity of 1-diazo-3-(2-methylcyclohexyl)-2-propanone (Compound F) is dissolved in 50 ml of tetrahydrofuran, 2.1 g of benzenesulfonic acid monohydrate is slowly added to the solution at room temperature, and the mixture is stirred until evolution of nitrogen ceases. The same procedure as in Example 3 is thereafter repeated to obtain 2.4 g of 1-benzenesulfonyloxy-3-(2-methylcyclohexyl)-2-propanone (Compound 17) in the form of a colorless transparent oil (yield: 77.4%).

EXAMPLE 6

Compounds 18 to 23 are prepared in the same manner as in Example 5.

EXAMPLE 7

Two grams of 1-chloro-3-ethyl-4-cyclohexyl-2-butanone (Compound i) is dissolved in 50 ml of acetone, 1.7 g of sodium iodide is added to the solution, and the mixture is stirred at room temperature for 5 hours. After the reaction, the insolubles are filtered off, the filtrate is distilled in a vacuum, and the oily product is dissolved in 50 ml of ether. The solution is washed with an aqueous hyposulfite solution, dried over anhydrous sodium sulfate and then distilled in a vacuum to remove the solvent. The resulting oily residue is dissolved in 50 ml of acetonitrile, 2.8 g of silver benzenesulfonate is added to the solution, and the mixture is stirred at room temperature for 12 hours. The reaction mixture is filtered to separate the insolubles off, the filtrate is concentrated in a vacuum, and the concentrate is subjected to extraction with 100 ml of chloroform. The extract is washed with water, dried over anhydrous sodium sulfate and then distilled in a vacuum to remove the solvent. The resulting oily product is subjected to silica gel column chromatography (developer solvent: chloroform) for separation and purification, giving 2.3 g of 1-benzenesulfonyloxy-4-cyclohexyl-3-ethyl-2-butanone (Compound 5) in the form of a colorless transparent oil (yield: 73.5%).

EXAMPLE 8

Compounds 7 to 9 are prepared in the same manner as in Example 7.

EXAMPLE 9

A 1.8 g quantity of 1-chloro-3-(4-methylcyclohexyl)-2-propanone (Compound iii) is dissolved in 50 ml of acetone, 1.45 g of sodium iodide is added to the solution at room temperature, and the mixture is stirred at room temperature for 6 hours. Subsequently 2.9 g of silver p-toluenesulfonate is added to the mixture, and the resulting mixture is stirred at room temperature for 24 hours. The reaction mixture is filtered to remove the insolubles, the filtrate is concentrated in a vacuum, and the resulting oily product is subjected to silica gel column chromatography (developer solvent: chloroform) for separation and purification, giving 2.3 g of 1-(4-methylcyclohexyl)-3-(p-toluenesulfonyloxy)-2-propanone (Compound 15) melting at 42° to 43.5° C. (yield: 74.2%).

EXAMPLE 10

Compound 16 is prepared in the same manner as in Example 9.

EXAMPLE 11

A 0.5 g quantity of trans-diazo-2-(4-isopropylcyclohexyl)-2-ethanone (Compound J) is dissolved in 30 ml of ether, an excess of benzenesulfonic acid is added to the solution, and the mixture is stirred until evolution of nitrogen ceases. The reaction mixture is washed with water, dried over anhydrous sodium sulfate and then distilled in a vacuum to remove the solvent. The residue is subjected to column chromatography (developer solvent: chloroform), affording 0.65 g of trans-2-(benzene-sulfonyloxy)-1-(4-isopropylcyclohexyl)-1-ethanone (Compound 25) melting at 48° to 49° C. (yield: 77.8%).

EXAMPLE 12

Compounds 24 and 26 to 38 are prepared in the same manner as in Example 11.

EXAMPLE 13

A 1.1 g quantity of trans-1-(hydroxyacetyl)-4-isopropylcyclohexane (Compound a) and 1.1 g of benzenesulfonyl chloride are dissolved in 1.5 ml of anhydrous dichloroethane, 1 ml of triethylamine is added dropwise to the solution at a temperature of up to 5° C. with ice cooling, and the mixture is thereafter stirred at up to 5° C. for 2 hours. The mixture is then poured into an ice-hydrochloric acid mixture, and the resulting mixture is subjected to extraction with 50 ml of chloroform. The extract is washed with water, dried over anhydrous sodium sulfate and then distilled in a vacuum to remove the solvent. The resulting oily product is crystallized from petroleum ether, and the crystals are recrystallized from ethanol to afford 1.5 g of trans-2-(benzenesulfonyloxy)-1-(4-isopropylcyclohexyl)-1-ethanone (Compound 25) melting at 48° to 49° C. (yield: 81%).

EXAMPLE 14

Compounds 27, 29, 31, 33, 35, 37 and 38 are prepared in the same manner as in Example 13.

Compounds of this invention are tested for pharmacological activities by the following methods.

1. Esterase Inhibiting Activity

A 10 micromole quantity of methyl butyrate in a 50% ethanol solution is added as a substrate to a specified amount of buffer solution (pH 8.0) containing 0.1 mole of trishydrochloric acid. To the mixture is further added a 50% ethanol solution of the compound of the invention, immediately followed by addition of an esterase solution prepared from a purified microsome fraction of the liver of a rat (adjusted to hydrolyze 9 micromoles of methyl butyrate at 37° C. in one hour). The mixture is reacted at 37° C. for 60 minutes.

After the reaction, alkaline hydroxylamine is added to the mixture to form a hydroxamic acid derivative of methyl butyrate, and a ferric salt is added to the derivative. The resulting red color is colorimetrically determined (at a wavelength of 540 nm) to determine the amount of remaining methyl butyrate. The esterase inhibiting ratios of the present compound at least at three concentrations are plotted as ordinate, and the logarithms of the concentrations as abscissa to obtain a line, which gives the 50% inhibition concentration ($IC_{50}$).

2. Chymotripsin Inhibiting Activity

Chymotripsin (0.1 unit) serving as an enzyme solution is added to a specified quantity of buffer solution (pH 8.0) containing 0.1 mole of trishydrochloric acid. To the mixture is further added a 50% ethanol solution of the compound of the invention. The mixture is reacted at 37° C. for 20 minutes.

On completion of the reaction, 10 micromoles of N-acetyl-L-thyrosine (ATEE) serving as a substrate is added to the mixture, and the resulting mixture is reacted at 37° C. for 30 minutes.

After the completion of the reaction, the amount of remaining ATEE is determined by the same hydroxamic acid method as above. The percent chymotripsin inhibition is given by $$\text{Percent inhibition} = \frac{A - B}{A} \times 100$$

wherein A is the amount of hydrolzed esters in the reaction system not containing the compound of the invention, and B is the amount of hydrolyzed esters in the reaction system containing the present compound.

3. Antilipemic Effect

Seven-week-old male Wister rats weighing 200 to 220 g are used, 5 rats in each group.

The compound of the invention (100 mg) is dissolved in 5 ml of olive oil. The olive oil containing the compound is orally given to the rat with a probe at a dose of 5 ml/kg. Two hours thereafter, 6 ml of whole blood is withdrawn from the descending aorta of the rat under ether anesthesia with a syringe containing heparin. The blood is centrifuged at 5° C. and 3000 r.p.m. to obtain the plasma. The plasma collected is used for determining the triglycerides content, using a triglycerides measuring kit (trade mark "Triglycerides-B Test Wako," product of Wako Junyaku Co., Ltd., Japan). Olive oil containing no compound is similarly given to a control group, while no treatment is conducted for a normal group. The triglycerides content in the plasma is also determined for these groups in the same manner as is the case with the test groups.

The percent hyperlipidemia inhibition achieved by the present compound is given by $$\text{Percent inhibition} = \frac{A - C}{A - B} \times 100$$

in which A is the triglycerides content of the control group, B is the triglycerides content of the normal group, and C is the triglycerides content of the group to which the present compound is given.

4. Acute Toxicity

Six-week-old male Wister rats weighing 180 to 200 g are used, 5 rats in each group. The present compound is suspended in a 5% aqueous solution of gum arabic, and the suspension is orally given to the rats. For one week after the start of the test, the rats are checked evey day for general toxicity symptoms, body weight and death to determine the $LD_{50}$ value.

The test results are shown in Table 6, in which TG stands for triglycerides inhibition.

TABLE 6

| Compound No. | Esterase $IC_{50}$ ($\times 10^{-6}$ mol) | Chymotripsin Inhibition (%) ($1 \times 10^{-4}$ mol) | Antilipemic effect IGI (%) | Acute toxicity (mg/kg) |
|---|---|---|---|---|
| 1 | 0.35 | 100 | 60 | >2000 |
| 2 | 7.8 | 90 | 50 | >2000 |
| 3 | 4.0 | 93 | 63 | >3000 |
| 4 | 23 | 78 | 52 | >3000 |
| 5 | 4.7 | 12 | 80 | >2000 |
| 6 | — | — | 52 | >3000 |
| 7 | 200 | 13 | 71 | >3000 |
| 8 | 0.8 | 31 | 73 | >3000 |
| 9 | 4.2 | 31 | 70 | >2000 |
| 10 | 3.5 | 22 | 46 | >3000 |
| 11 | 7.2 | 19 | 60 | >3000 |
| 12 | 1.0 | 24 | 39 | >3000 |
| 13 | 20 | 50 | — | >2000 |
| 14 | 40 | 40 | 81 | >3000 |
| 15 | 1.4 | 94 | 85 | >2000 |
| 16 | 5.0 | 81 | 11 | >3000 |
| 17 | 0.032 | 97 | 72 | >2000 |
| 18 | 8.4 | 72 | — | >2000 |
| 19 | 5.4 | 57 | 74 | >3000 |
| 21 | 6.0 | 94 | 70 | >3000 |
| 22 | 0.2 | 58 | 59 | >2000 |
| 23 | 1.4 | 24 | 67 | >3000 |
| 24 | 0.7 | 16 | 60 | >3000 |
| 25 | 0.065 | 62 | 90 | >3000 |
| 26 | 11.0 | 14 | 50 | >3000 |
| 27 | 2.0 | 35 | 76 | >3000 |
| 28 | 1.2 | — | — | >3000 |
| 29 | 0.13 | — | — | >3000 |
| 30 | 4.0 | 30 | 57 | >3000 |
| 31 | 1.6 | 43 | 79 | >3000 |
| 32 | 0.56 | 13 | 61 | >3000 |
| 33 | 0.17 | 19 | 76 | >3000 |
| 34 | 4.6 | — | 52 | >3000 |
| 35 | 4.6 | — | 72 | >3000 |
| 36 | 86.0 | 44 | 52 | >3000 |
| 37 | 5.4 | 22 | 66 | >3000 |

Preparation examples of this invention are given below.

PREPARATION EXAMPLE 1

The following composition is enclosed in soft capsules in an amount of 500 mg in each capsule.

| | |
|---|---|
| Compound 25 | 250 mg |
| Olive oil | 250 mg |

PREPARATION EXAMPLE 2

The following composition is enclosed by the same method as above in soft capsules in an amount of 500 mg in each capsule.

| | |
|---|---|
| Compound 8 | 250 mg |
| Olive oil | 250 mg |

PREPARATION EXAMPLE 3

Tablets, each weighing 406 mg, are prepared from the following composition.

| | |
|---|---|
| Compound 7 | 100 mg |
| Soft silicic anhydride | 80 mg |
| Crystalline cellulose | 140 mg |
| Lactose | 80 mg |
| Talc | 2 mg |
| Magnesium stearate | 4 mg |

PREPARATION EXAMPLE 4

Tablets, each weighing 406 mg, are prepared from the following composition in the same manner as above.

| | |
|---|---|
| Compound 37 | 100 mg |
| Soft silicic anhydride | 80 mg |
| Crystalline cellulose | 140 mg |
| Lactose | 80 mg |
| Talc | 2 mg |
| Magnesium stearate | 4 mg |

PREPARATION EXAMPLE 5

Suppositories, each weighing 2000 mg, are prepared from the following composition.

| | |
|---|---|
| Compound 33 | 1000 mg |
| Witepsol W-35 (trademark) | 1000 mg |

PREPARATION EXAMPLE 6

Suppositories, each weighing 2000 mg, are prepared from the following composition in the same manner as above.

| | |
|---|---|
| Compound 31 | 1000 mg |
| Witepsol W-35 | 1000 mg |

PREPARATION EXAMPLE 7

Granules as enclosed in an amount of 1000 mg with a wrapper are prepared from the following composition.

| | |
|---|---|
| Compound 27 | 200 mg |
| Soft silicic anhydride | 170 mg |
| Crystalline cellulose | 350 mg |
| Lactose | 270 mg |
| Magnesium stearate | 10 mg |

PREPARATION EXAMPLE 8

Granules as enclosed in an amount of 1000 mg with a wrapper are prepared from the following composition in the same manner as above.

| | |
|---|---|
| Compound 36 | 200 mg |
| Soft silicic anhydride | 170 mg |
| Crystalline cellulose | 350 mg |
| Lactose | 270 mg |
| Magnesium stearate | 10 mg |

PREPARATION EXAMPLE 9

An elixier as contained in an amount of 20 ml in a vial is prepared from the following composition.

| | |
|---|---|
| Compound 25 | 300 mg |
| Ethanol | 0.5 mg |
| Granular sugar HCO-60 | 2000 mg |
| Flavor | 0.01 ml |
| Purified water | q.s. 20 ml |

We claim:

1. A sulfonate derivative represented by the formula

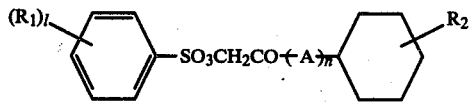

wherein $R_1$ is lower alkyl, lower alkoxy or halogen, $l$ is an integer of from 0 to 3, n is 0 or 1, A is straight-chain or branched-chain alkylene having 1 to 4 carbon atoms, and $R_2$ is hydrogen or lower alkyl but, when n is 0 or 1 and A is straight-chain alkylene with 1 to 4 carbon atoms, is not hydrogen.

2. An antilipemic composition comprising an effective amount of a sulfonate derivative represented by the formula

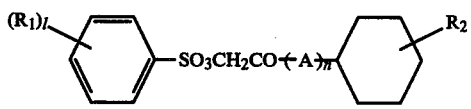

wherein $R_1$ is lower alkyl, lower alkoxy or halogen, $l$ is an integer of from 0 to 3, n is 0 or 1, A is straight-chain or branched-chain alkylene having 1 to 4 carbon atoms, and $R_2$ is hydrogen or lower alkyl but, when n is 0 or 1 and A is straight-chain alkylene with 1 to 4 carbon atoms, is not hydrogen and a pharmaceutically acceptable diluent.

* * * * *